United States Patent [19]

Neumeyer

[11] Patent Number: 4,684,555

[45] Date of Patent: Aug. 4, 1987

[54] DENTAL RETENTION PINS

[76] Inventor: Stefan Neumeyer, Leminger strasse 10, 8491 Eschlkam, Fed. Rep. of Germany

[21] Appl. No.: 827,450

[22] Filed: Feb. 10, 1986

[30] Foreign Application Priority Data

Jun. 25, 1985 [DE] Fed. Rep. of Germany ......... 352266
Sep. 2, 1985 [DE] Fed. Rep. of Germany ....... 3504472

[51] Int. Cl.$^4$ .................. B32B 15/00; B32B 9/00; A61C 8/00
[52] U.S. Cl. ...................................... 428/36; 428/432; 428/469; 433/201.1; 433/202.1; 433/220; 433/222.1
[58] Field of Search .................. 433/201.2, 202.2, 220, 433/222; 428/36, 432, 469

[56] References Cited

U.S. PATENT DOCUMENTS

| 3,829,973 | 8/1974 | Masuhara et al. | 32/15 |
| 4,028,325 | 6/1977 | King et al. | 260/42.15 |
| 4,355,978 | 10/1982 | Ericson | 433/220 |
| 4,398,007 | 4/1983 | Kubota et al. | 526/273 |
| 4,443,494 | 4/1984 | Gonser | 156/64 |
| 4,514,174 | 4/1985 | Dougherty et al. | 433/226 |

FOREIGN PATENT DOCUMENTS 475999 6/1915 France .
343061 1/1960 Switzerland .

OTHER PUBLICATIONS

APM-Sterngold 6-25-84.

Primary Examiner—John L. Goodrow
Assistant Examiner—Patrick J. Ryan
Attorney, Agent, or Firm—Charles W. Fallow; Martin P. Hoffman; Mitchell B. Wasson

[57] ABSTRACT

A dental retention pin preferably made of metal is provided with a closed, cylindrical coating of bond assisting material, and an additional layer of a plastics filling material in order to obtain a physical-chemical or a purely chemical bond between the retention pin and the filling structure for obtaining a substantially increased retention power compared with known metal pins, which merely result in a mechanical or mechanical-physical joint to the filling structure. The retention force will be increased by shrinking the bond assisting layer or the outermost plastics layer onto said bond assisting layer around the pin so that the layer spans itself around the pin in a ring-like manner. Furthermore, examples for the structure of a retention pin are described, which improve the handling and insertion of such retention pins by the dentist considerably.

25 Claims, 24 Drawing Figures

DENTAL RETENTION PINS

BACKGROUND OF THE INVENTION

This invention refers to dental retention pins comprising a first section, which is to be inserted or screwed into the tooth, and a second section, which extends from the tooth into the space for the filling structure and which improves the retention to the tooth.

Dental retention pins are used for the restoration of teeth in order to obtain a main or an additional retention for the filling structure within the remainder of the tooth structure, which is called ivory. A pin is inserted, preferably screwed into a borehole of the tooth with one section, whereas the other section extends from the tooth and is embedded into the filling material around the pin. Metal pins result in a mechanical joint with the filling structure; therefore that part of the pin which is embedded into the filling structure for improving said mechanical joint with the filling material is provided with screw-like or any other positive or negative macroscopic deformations so that the filling material, especially under tension and compression forces, cannot separate from the pin. Because the filling material under chewing conditions undergoes considerable stresses, such as tension and compression forces, this type of mechanical joint, which does not allow an exact body contact between pin and filling structure, in general is not sufficient. Between the filling material and the pin an edge gap is formed. Locations at which the pin does not have a firm and complete contact with the filling material over the full surface are positions of weakness, which do not add to the stablility and durability of the filling (or alternatively, the joint between the filling and the tooth) and result in fast aging of the plastics material or the filling material in these areas. This which decreases the retention of the pin continuously with increasing time. Therefore, this method, which up to now is used extensively, is not satisfactory. As filling materials nowadays preferably amalgams, plastics filling materials and glass ionomer cements are used. A chemical bond, which would overcome these disadvantages, up to now only can be obtained if pins plated with gold or silver are used and if amalgam is used as a filling material. However, because amalgam fillings in the field of teeth restoration are more and more being replaced by other types of filling materials, because plastics materials as well glass ionomer cements (in addition to the main field of use within the front teeth area) are being used in the lateral teeth area, the forementioned method is of decreasing importance. This is so because the joint between a retention pin made of metal or other material and the filling mass made from platics material or from glass ionomer cement or from other non-metallic materials generally results in an exclusively mechanical joint.

A mechanical joint has considerable disadvantages compared with chemical or alternatively physical-chemical bondings, because with a mechanical joint micro-edge-gaps are obtained, which allow very small relative movements between pin and filling material. Because liquid and bacteria are able to enter such gaps they cause corrosions and aging of the filling materials, as well the danger of secondary caries. Furthermore, it is to be expected that the filling materials will cause coloration and that the dark metal pin will shine through. Finally and especially, the retention power of a pin with a mechanical joint to the filling material is lower by far than a chemical bond or a physical-chemical bond under the wet conditions within the mouth, and will decrease with continuous aging of the plastics material, as detailed investigations of the inventor have shown. This problem is still more serious if such pins will be used for teeth-superstructures and if structure material is to be ground and insufficient thickness of material will be left in order to support the pin and to provide a correct joint.

The problem of micro-edge-gaps within the compound plastics/metal has been known for a long time in the dental field. One solution for this problem is the use of an inorganic intermediate layer as a bond assisting layer, which results in a chemical bond to the substrate and to the plastic material. On a metal surface, which preferably is treated by sandblasting, an $SiO_x$-C layer, on top of it a silane bond assisting layer, and on top thereof a plastics layer, are applied. The bond assisting layer provides the chemical bond between the plastics material and the $SiO_x$C layer. This type of plastics/metal-compound in the dental field up to now has been used exclusively for larger, substantially plane surfaces, namely in connection with crown structures and bridge structures within the crown area, in order to face a metal surface with plastics material. The bonding surface always has a relatively large surface area, and the plastics material is the outermost, which means the visible side of the completed tooth. This plastics material also will have to meet the requirements for high surface quality (amenability to receive polish, density, etc.).

SUMMARY OF THE INVENTION

It is an object of this invention to provide dental retention pins having a satisfying physical-chemical or chemical bond between the surface of the pin and the filling structure in addition to or independent from the mechanical joint.

It is a further object to increase the stability of the bond between the pin and the filling material considerably.

Another object of this invention is to keep the effective bonding area as small as possible, and substantially smaller than with pins which are available nowadays.

It is another object to effectively prevent any micro edge gaps between the pin surface and the material of the filling structure.

A still further object of this invention is to reduce early aging of the filling material, caused by the perculation between the filling material and the metal pins.

Finally, it is an object of this invention to provide a retention pin mechanically in such a manner that inserting a pin into the tooth to be restored is most simple and useful.

According to the invention these, objects and problems are solved by providing the pin for increasing retention force (at least on its portion facing the filling structure) with a cylindrical or cup-shaped layer comprising of at least one bond assisting material, which allows a physical-chemical or chemical bond between the material of the pin and the material of the filling structure, which is applied to the pin and which is resistent to the conditions of the wet mouth.

Basically, this invention refers to two different types of retention pins. One type of retention pin is ready-made for the dentist and is supplied with a complete casting so that the dentist merely needs to insert the pin into the tooth of the patient and to build up the filling structure around this pin. The other type of pin is mechanically treated, but, does not have a proper coating applied to it; rather, the coating material is supplied to the dentist separately. In the latter case the dentist inserts the pin without coating into the tooth, applies the coating material to the pin himself and finally builds up the filling structure upon the pin on the tooth. In the following description reference is mainly made to the ready-made pin, which is preferred for industrial production.

With a cylindrical coating according to this invention on the retention pin, it is possible to increase severalfold the retention power from metal to plastics material by means of bond assisting layers compared with plane, relatively large areas, namely from 10–20 N/mm$^2$ (Newton/square millimeters) to 50–70 N/mm$^2$. This considerable increase results from the fact that around the annular surface, which has been made microretentive as by roughening the surface, the shrinkages obtained during polymerisation of the available plastics and glass ionomer materials through the bond assisting layer cause very high bracing effects, which lead to the high retention values of 50–70 Newtons per square millimeter of pin surface. Examples for plastics materials used herewith are Adaptic, Durafill, PMNA-Plastics, BIS-GMA-Plastics, polyurethanes and the like, which will undergo a chemical bond with the filling structure. The shrinking process either takes place within the filling material itself or within the bond assisting layer applied to the pin. With bond assisting layers and filling materials, plastic materials or alternatively glass ionomer cements, which are available nowadays, this process is most important, because the retention forces can be increased extraordinarily. Theoretically, the bonding energies of physical or chemical bonding mechanisms are very high; however, they cannot be used practically. The higher the stability of the chemical bond, the less important the additional retention by the shrinkage process will be. Even with extraordinary improvement of the chemical bond assisting materials, the cylindrical shape of the coating is most important. This is so because only the closed circular shape allows the pin to take up the compression, tension, rotational and shearing forces, which act in all directions as the tooth is stressed during chewing, over its entire surface, and accordingly will be able to meet its task of anchoring the filling structure qualitatively and quantitatively better than with mechanical systems. This ringlike or cylindrical arrangement is still more important if the pins will be used for restoring badly damaged teeth with subsequent removal of material, such as grinding for a crown. Removing too much material has the result that the material around the pin (with mechanical anchorage) at certain points will be too weak to take up compression forces so that the pin will no longer be able to meet its retentive task at certain directions of stresses. Opposite thereto, according to the bonding principles of the subject invention the pin area opposite to the impact of the force will be stressed by tension and thus, will be effective as a retention.

The retention forces of pins with physical-chemical or purely chemical bonding are, as detailed experiments by the inventor have proven, considerably higher than those obtained by mechanical retention systems using threads so that with this invention it will be possible to refrain substantially from using additional macroscopic retentions in the form of extensions, undercuttings and the like. However, if pin shapes will be used, which are different from the cylindrical shape with micro retentions, such shapes mainly will be used in order to avoid excessive tensions, which are generated within the filling material and are characteristic for the corresponding shape of restorations.

The coating on retention pins according to this invention can be formed in different manners. It is most important that the coating embraces the total cylindrical surface of the pin (or the entire pin) completely so that a coating will be obtained, which is continuous in a peripheral direction over the pin. Basically, this invention refers to completed retention pins with applied coating according to the following embodiments:

1. A siliciumoxide-carbon-layer is applied to the retention pin, for example according to the so-called silicoater method. This layer results in an intimate adhesive physical bond with the surface of the pin, which pin preferably is made of metal and the cylindrical surface of which is roughened, as by sandblasting. Onto said SiOx-C-layer a silane bond assisting substance is applied, which results in a chemical bond to the plastics material, which is the outermost layer of the completed retention pin and which undergoes a chemical bond with the material of the filling structure.

2. With a different embodiment of this invention a tin oxyde layer or a correspinding metal oxide layer is applied onto the roughened retention pin, and upon said layer a tin oxide, titanium oxide or the like bond assisting layer is applied, upon which as the outermost layer a coating of plastics material is provided. The bondings between the layers are chemical bonds. Alternatively, instead of a tin oxide a sparingly soluble tin sulfide or alternatively, instead of titanium oxide a titanium sulfide can be used, which may result in better reactions with the bond assisting layer.

3. With a further embodiment of this invention the retention pin is made from titanium or corresponding material, which forms a titanium oxide or the like at the surface, or alternatively generates said oxide by means of a special process. Onto said titanium oxide a bond assisting layer and upon the latter plastics material is applied. Instead of titanium other metals or alloys thereof can be used as a material for the retention pin the surfaces of which are oxydized and which are biocompatible as well non-corroding in alloys. Also metal alloys, for example a Ti-Va-Al-alloys can be used. Examples for a bond assisting layer, which can be used in this manner, are titanates or the 4-metal-opaque-resin (which already includes the opaquer).

4. According to a further embodiment a porcelain mass is applied to a retention pin, and on top of it a suitable bond assisting layer, f.e. a silane bond assisting layer is applied, which results in a chemical bond with the layer of plastics material applied to the bond assisting layer. The plastics material layer, which forms the outermost layer of the retention pin, causes a chemical bond to the material of the filling structure.

Basically, in addition to the plastics material layer an opaquer layer can be applied to the retention pin, which opaquer layer determines the colour of the completed retention pin. However, usually opaquer layer and plastics material layer are formed and applied as one layer.

So far as it concerns retention pins, with which the metal is without a coating and with which the coating is applied to the pin by the dentist there are in essence the following possibilities:

1. The retention pin is made of metal and has a roughened surface of porcelain around its entire cylindrical surface. The dentist applies a suitable bond assisting layer, such as a silane bond assisting layer before or subsequent to inserting the pin into the borehole of the tooth, and on this layer a layer of filling material is applied. The advantage of this chemical compound through the porcelain mass is that the porcelain already is coloured with the tooth colour, that it is resistive to the conditions of the wet mouth, is inert and is of high stability.

2. On a metal retention pin, for example made of steel, the surface of which is provided with micro retentions, either mechanically by roughening, or chemically, a metal oxide comprising a metal which is different from the metal of the retention pin (for example, titanium oxide) is applied, on top thereof a suitable bond assisting layer, which is titanate for titanium oxyde, and on top of that a plastics material or opaquer layer is applied.

3. A metal pin is used, which on its microretentive surface is provided with a metal oxyde layer the metal of which is the same as the metal of the retention pin. The metal oxide either forms itself on the pin surface or is formed by suitable processes. Again, a suitable bond assisting layer is applied onto the metal oxide, and on top thereof a plastics material or opaquer layer is formed. A suitable metal is titanium, which has a coating made of titanium oxyde; the bond assisting layer then wil be titanate. Instead of using metal oxydes as described above under 2. or 3. metal sulfides can be used.

With special embodiments bond assisting layer and opaquer-plastics-material-layer can be applied as one layer. However, it can be advantageous to apply the bond assisting layer, the opaquer layer and further opaquers from plastics material in separate steps or layers, if by doing so the retention can be improved. It can also be advantageous to choose the layers different in their composition, as concerning the size of the filling particles or the like, in order to be able to control the parameter, forexample temperature sensitivity, physical characteristics as attenuation, bonding etc.; for example silicium oxyde particles can be used as filling particles.

With all metal pins according to this invention it is necessary to obtain a proper chemical bond to provide the cylindrical surface of the pin with microretentions before applying a bond assisting layer onto the surface, which microretentions either are obtained chemically by providing pores, or in a mechanical manner by sandblasting or the like. Macroscopic forms on the surface of retention pins according to this invention generally are not for improving the retention, but for taking up tensions within the filling structure. In a special case the plastics material layer includes calcium-aluminum-fluor-silicate particles including natrium, which results in a bond to the glass ionomer cements of the filling structure.

If pins made from unnoble materials, such as titanium, are used for the filling material amalgam, a chemical bond to the filling material amalgam can be obtained by means of a coating made from gold, silver or platin, Initially, a noble metal layer forming the bond assisting layer will be applied to the pin surface, on top thereof a very thin attenuation layer (0.5-100 $\mu$m) from tin (according to the characteristics of the amalgam and onto this layer a noble metal layer will be applied, which results in a positive bond to the amalgam of the filling structure. If the outer layer will be damaged, the layer underneath bonds with the filling material so that the outer layer of noblemetal always will be reactive. The outermost layer of the pin also can be an amalgam layer, which acts as a protective layer.

If adhesives will be used as bond assisting layers, f.e. polyurethane adhesives, they are required to be hydrolytically stable, to be applied cylindrically onto the pin and to brace themselves around the pin by shrinking in order to obtain a high retention force. The adhesive layer can be provided with an impermeable plastics material layer, which bonds chemically with the adhesive and which prevents the entrance of moisture to the inner surface of the pin.

DESCRIPTION OF THE PREFERRED EMBODIMENTS

Figure 1:
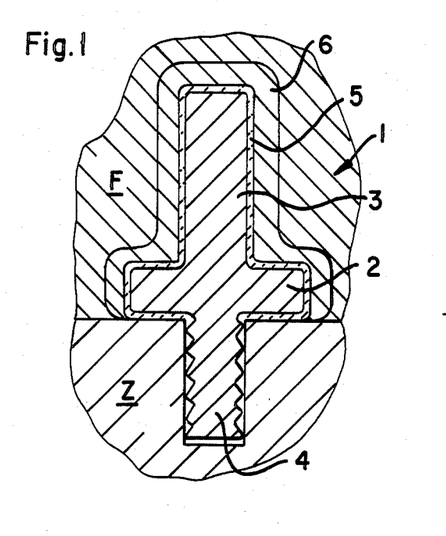
FIG. 1 is a schematatic sectional view through a dental retention pin according to this invention with a coating applied to the pin surface.

Retention pin 1 is provided with a flange 2, which when being inserted into the bore of a tooth, is used as a stop towards the tooth substance Z, and which divides pin 1 into an upper section 3, which is embedded within the filling structure S, and into a lower section 4, which is inserted, preferably screwed into a borehole of the tooth substance Z. Pin 1 has a bond assisting layer 5, f.e. metal ceramic or alternatively porcelain mass on its entire surface, at least on its upper section 3 and around flange 1. Retention pin 1 is available to the dentist for restoration of teeth in this shape. In order to protect the bond assisting layer 5 before completing the pin and inserting it into the tooth to be repaired, pin 1 can be provided with a protective layer 6, which can be an opaquer at the same time, or is packed up at the place of production in an inert atmosphere ready for shipping, whereby the package only will be opened by the dentist before the pin is to be used. The bond assisting layer undergoes a chemical bond with the filling mass characterised by F, which is applied by the dentist onto the tooth substance and around pin 1, whereas a metal pin 1 without any bond assisting layer would not be able to react chemically with the material of the filling structure, and merely would result in a mechanical joint.

Figure 2:
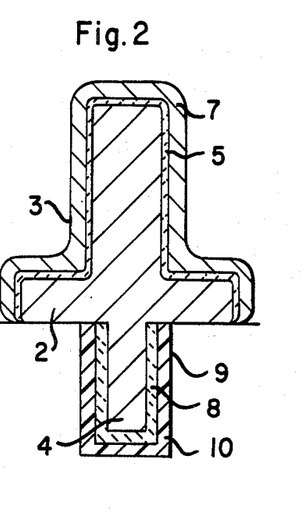
FIG. 2 is a schematic sectional view through a retention pin according to this invention with a special structure of the lower pin section.

With the embodiment according to FIG. 2 the upper section 3 with flange 2 of the retention pin 1 is provided with an opaquer layer 7 on the outer surface of the bond assisting layer 5, which opaquer layer is a body material preventing that with the completed retention pin 1 provided with a coating the metal pin 3, 4 would shine through. With this opaquer layer 7 the completed retention pin 1 can be given any colour or any appearance. At the same time the opaquer layer is used as a protective layer for the bond assisting material. With the embodiment according to FIG. 2 the lower section 4 of the retention pin is formed as a variation, which also can be used for other shapes according to the various figures independent from the type of coating on the upper section 3. Pin portion 4 is coated with a metal oxide layer 8, whereas the surfaces of the bore 9 within the tooth substance Z are coated with a glass ionomer cement layer 10 so that the glass ionomer cement will undergo a firm bond with the metal oxide layer when the retention pin 1 is inserted into the tooth substance. Lower section 4 can be shaped as a cylinder, and can be provided with threads, which are common with this type of retention pins and which in addition can result in a mechanical connection of the screw pin to the tooth substance Z. Basically, a plastics sleeve can be pushed over the coating of the retention pin, which sleeve protects the coating material.

Figure 3:
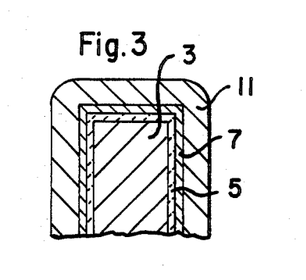
FIGS. 3–6 are schematic sectional views of different variations each of an upper section of a dental retention pin according to this invention with different coatings each applied to the pin surface.

The embodiment of a retention pin according to FIG. 3 differs from that according to FIG. 2 in view of the layer 11 of filling material applied onto the opaquer layer 7. FIG. 3 as well the embodiments according to FIGS. 4-7 only show the upper section 3 of the retention pin. The filling material 11 preferably is the same material as the filling material of the filling structure F, which undergoes a chemical bond between the retention pin 1 inserted into the tooth substance for restoration, and the material of the filling structure. The completed retention pin 1, therefore, is already provided with part of the filling material on its portion extending from the tooth substance; on the other hand the filling material 11 and the material of the filling structure F can be different filling materials, as long as they result in a good and firm bond, when the dentist builds up the filling over the retention pin 1 and the tooth substance.

Figure 4:
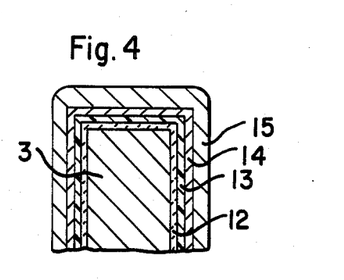

The embodiment of a retention pin according to FIG. 4 starts from a retention pin 1, onto which for example a silicium oxide-carbon-layer 12 is applied, which is coated with a silane bond assisting layer 13, which is covered outwardly by an opaquer layer 14 and a filling material layer 15 as the outermost layer. Layer 12 can be applied by the so-called silicoater method to the surface of metal pin 1 or 3. The silane bond assisting layer 13 bonded with layer 12 results in a firm chemical bond to the filling material layer 15, which is a layer of plastics material, whereby the opaquer layer 14 either is arranged intermediate or alternatively is integrated into the silane bond assisting layer 13 or into the filling material 15.

Figure 5:
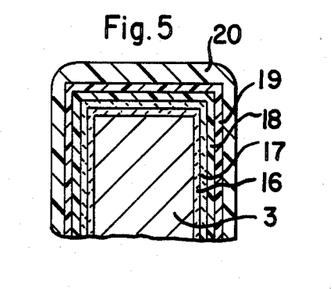

A retention pin 1 according to FIG. 5 is provided on its upper section 4 with a tin oxide layer 16, an aluminum oxide layer (or silicium oxide layer 17) applied to the tin oxide layer 16, and a following bond assisting layer 18, to which a further bond assisting layer 19 as well an outermost plastics material layer 20 is applied. Providing two or several bond assisting layers is recommendable, if predetermined parameters are to be controlled, for example in order to obtain a better adhesive power, an attenuation, a balance of predetermined parameters, etc. Within the preceeding examples also an additional opaquer layer can be provided in a corresponding manner, which opaquer layer is formed in one layer or in a number of layers. Instead of a tin oxide layer 16 and an aluminum oxide layer 17 also other layers of ceramic material, porcelain and the like are applied, burnt on, sputtered or the like, without deviating from the basic idea of this invention.

Figure 6:
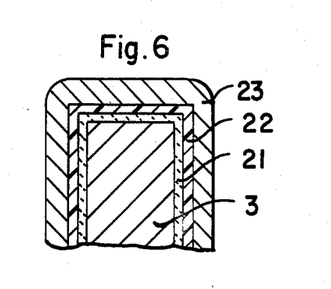

According to a further embodiment of a retention pin shown in FIG. 6 a tin oxide layer 21 is applied to the upper section 3, an opaquer-compound system is applied to the bond assisting layer 22, and the filling material 23 is applied to the opaquer compound system as the outermost layer.

Instead of a metal pin 1 a pin made from plastics material, porcelain, ceramics or the like can be used. Bond assisting layer, opaquer layer and filling material are applied to these types of pins in a manner similar to the one described with metal pins, whereby the materials of the layers will be adapted to the characteristics of the pin compound.

The bond assisting layer can be substituted by an adhesive layer if said adhesive layer will be able to meet the requirements that the adhesive maintains its adhesive power completely or nearly completely within the wet conditions of the mouth. This type of adhesives can be an epoxyd resin, polyurethane or corresponding special purpose adhesives, as they are known in many fields of technique. With this type of adhesive it can be useful to apply an impervious layer of plastics material onto the adhesive, which bonds chemically with the adhesive in order to seal the adhesive against the wet conditions of the mouth. In order to obtain the required high retention force with this type of adhesives it is most important that the adheisve is applied cylindrically around the entire upper section and shrinks towards the pin.

Figure 7:
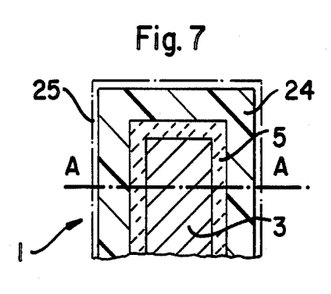
FIG. 7 is a schematic sectional view similar to FIGS. 1–6 of a general embodiment of this invention.
Figure 8:
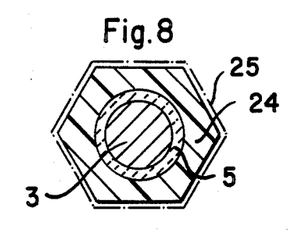
FIG. 8 is a schematic sectional view through a pin structure according to FIG. 7, along line A—A

FIGS. 7 and 8 show a general and basic embodiment of a retention pin according to this invention. The upper section 3 of pin 1, which is made of metal, plastics, ceramics or the like material, according to FIG. 7 is provided with an outer layer 24, for example a protective layer, which embraces the underneath bond assisting layer 5 or other layers provided between layer 24 and bond assisting layer 5, and which is the plastics layer forming the chemical bond to the filling structure.

The outer cylindrical surface of the protective layer 24 is—as shown in FIG. 8—formed as a head for a rotating tool or screwing tool, f.e. as a hexagon for taking up a head screw spanner 25 (dash-dotted line) or as (not shown) a slot for taking up a screw driver by means of which the pin is screwed into the tooth substance.

Figure 9:
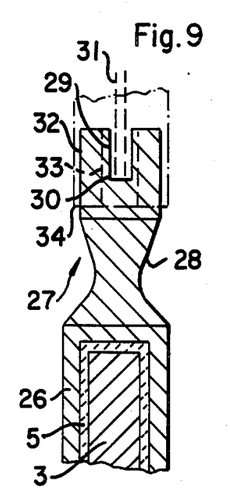
FIG. 9 is an embodiment of the pin with a schematically shown screwing device at the screw head.

According to FIG. 9 the outermost layer 26 of the above section 3 of the coating of pin 1 is formed so that it has an extension 27 extending outwards from pin 1, which extension is an integral constituent of layer 26 and which has a breaking point 28. Extension 27 is provided with a slot 30 on its face 29 for taking up a screw driver 31, or alternatively is provided with a polyhegonal head 33, for taking up a head screw spanner (dash-dotted line) or the like. When screwing-in the pin by means of a screw driver or a head screw spanner the pin is screwed into the bore hole 9 with its lower (not shown) section 4 to such an extent that the lower side of the flange 2 contacts the upper side of the prepared tooth substance surface. Screwing the extension 27 further into the hole 9 causes breaking the extension 27 from the retention pin 1 at the breaking point 28 so that extension 27 can be removed by the dentist.

Figure 10:
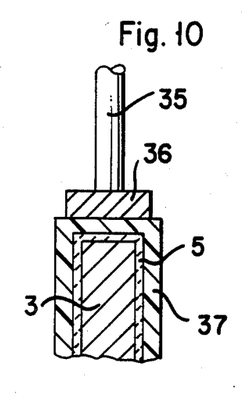
FIG. 10 is a further embodiment of a pin with a different embodiment of a screwing device.

With an embodiment according to FIG. 10 similar to the embodiment of FIG. 9 the extension 35, which is actuated by rotational tool, is provided with a carrier or alternatively a plate 36, as a metal plate, which is fastened to the extension 35. Plate 36 is fixed to the face of the outer layer 37 in such a manner, for exmple by adhesive, that similar to a breaking point extension 35 and plate 36 separate from the outer layer 37, when the retention pin is screwed into the tooth substance and contacts the stop; then, the pin remains within the tooth substance, and extension 35 and plate 36 can be removed together.

Figure 11:
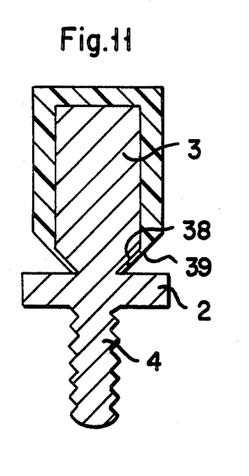
FIG. 11 is a longitudinal sectional view through a retention pin with screwing head and screwing tool.

FIG. 11 shows a shape of a pin, with which the upper section 3 where joining the stop plate 2 forms a throat, by means of which the dentist is in a position to bend the upper pin section 3 from the direction along the longitudinal axis into a required inclined position. However, throat 38 can be dispensed with and it can be sufficient merely to provide the throat 39 of the outermost plastics layer, preferably if the plastics layer has a relatively large diameter.

Figure 12:
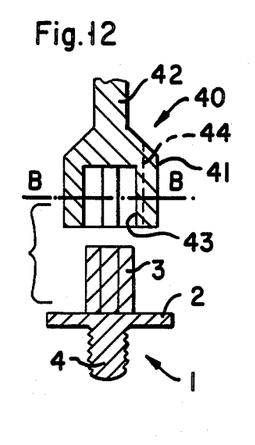
FIG. 12 is a schematic sectional view along line B—B.

The embodiment according to FIG. 12 shows a retention pin 1 with an upper section 3 and a lower section 4. Upper section 3 is formed as a hexagonal head, as shown in FIGS. 7 and 8. Tool 40 is a socket 41 with head 42 the hexagonal opening 43 of which receives the head 3 of the pin up to the stop flange 2. Tool head 41 is provided on its shell with a slot 44 extending parallel to the direction of its axis and forming a breaking point, which breaks when inserting the pin 1 by means of a screwing tool acting upon shaft 42, if the resistance will be sufficient, for example, if flange 2 contacts the tooth substance.

Figure 13:
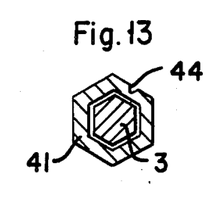
FIG. 13 is a cross-sectional view similar to FIG. 12 in the split condition.
Figure 14:
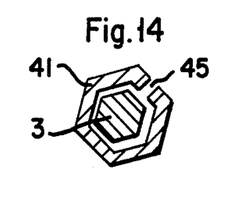
FIG. 14 is a further embodiment of a retention pin in longitudinal section.

FIG. 13 shows a cross-section B—B through the tool and the pin head at the beginning of the screwing operation, FIG. 14 the tool head subsequent to the breakage. The breaking of the material of the head results in a gap 45, tool 41 separates from the pin head 3 and can be removed.

Figure 15:
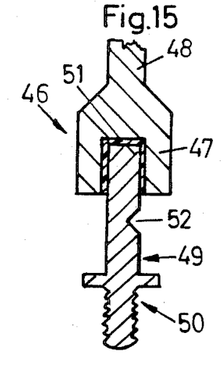
FIG. 15 is a schematic view of a further embodiment of a screwing tool.

FIG. 15 shows an embodiment of a pin screwing tool, with which tool 46, which comprises the tool head 47 and the shaft or alternatively sleeve 48 (as well not shown manual or motor drive), is put on an extended upper section 49 of pin 50, and tool head 47 as well upper end of section 49 are fastened together, for example are bonded at 51 at least over an essential part of the common contact surface. Section 49 has a breaking point 52, at which the upper section 49 breaks, when pin 50 on being screwed into the tooth meets a corresponding resistance. That part of section 49 above the breaking point, which is fastened to the tool head and the tool shaft, is removed after breaking. Instead of an adhesive bond, a joint 51 also can be a pressing joint.

Figure 16:
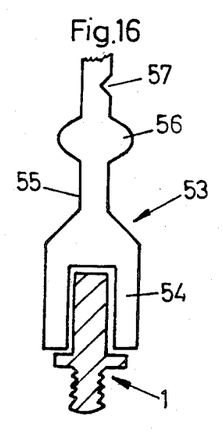
FIG. 16 is a schematic view of a further embodiment of a screwing tool with retention pin.

FIG. 16 shows an embodiment with which retention pin 1 similar to that according to FIG. 12 is provided with an upper section 3 as a head portion. Tool 53 comprises a head 54 embracing the pin head 3, a shaft 55 with a bulge 56 along the shaft, and a breaking point 57. If in inserting the pin into the tooth a critical resistance value will be obtained the shaft breaks at 57. Part 53 of the tool remaining on the pin can be withdrawn from pin 1. This type of tool 53 is a one-way tool so that tool 53 and pin 1 are sold as a unit and tool 53 is thrown away after use.

Figure 17:
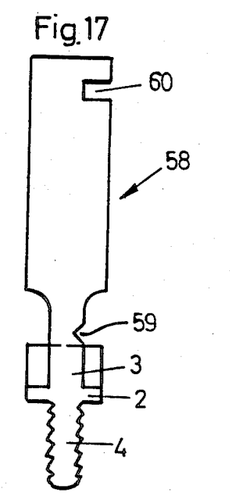
FIG. 17 is an embodiment of a retention pin with integrated screwing tool.

A different embodiment of a one-way tool is shown in FIG. 17. Pin 1 and tool 58 are formed as an integral unit. Tool 58 is provided with a breaking point 49 adjacent the upper restriction of pin 1, where tool 58 breaks away from the pin if when screwing the pin a critical resistance value will be obtained. 60 is a recess, which is used for inserting a usual angle-piece for the driving operation.

Figure 18:
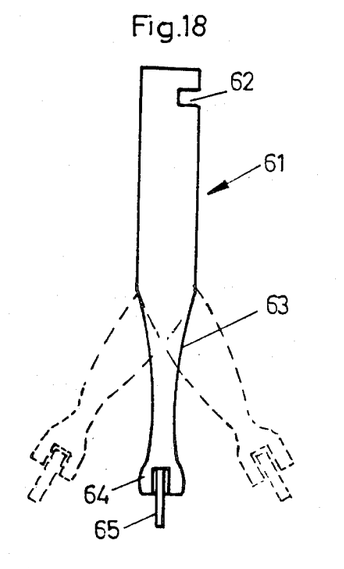
FIG. 18 is a schematic view of a screwing tool with flexible shaft.

With the embodiment according to FIG. 18 tool 61 with its recess 62 for taking up the angle-piece is provided with a shaft 63 and a cap head 64 with a recess for taking up retention 65. Tool 61 inclusive the cap head 64 has a flexible shaft 63 so that the shaft with the cap head 64 and the pin 65, which is fastened therein, can be deflected to all sides, as shown in dotted lines in FIG. 18. In its deflected condition (dotted lines) a proper positioning of the tool towards a borehole within the tooth substance is possible in an angle to the vertical axis of the tool.

Figure 19:
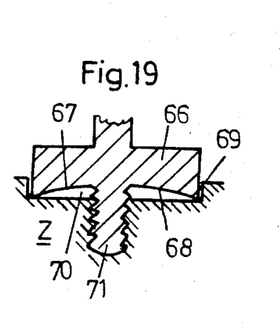
FIG. 19 is a detailed view of a special embodiment of a compression plate of a retention pin according to this invention.

FIG. 19 shows a special embodiment of the underside of the pin flange 66 facing the tooth substance. Accordingly, the underside 67 is inclined inwardly and upwardly, whereby the incline can be straight or curved (shown with 68). For taking up flange 66 the tooth substance has a bore 69, which together with the underside of the flange results in a free space 70. In view of this structure the tooth substance is urged inwardly against flange 66 and the lower section 71 of the retention pin, so that an increased contact force of the dentine (=tooth substance material) at the pin, an increased retention force and a decreased perculation gap will be obtained. Furthermore, by increasing the pressure a compression of the tooth substance can be obtained; this allows easier shearing at the breaking point and avoiding stresses acting in the lower areas of the tooth substance.

Figure 20:
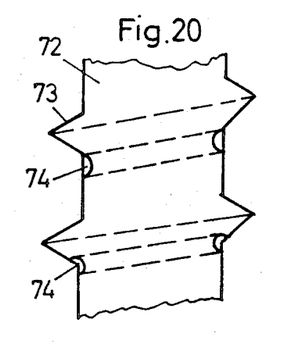
FIG. 20 is a schematic view of a special embodiment of a shaft of the retention pin to be screwed into the tooth substance.

With the embodiment according to FIG. 20 the lower shaft 72 (according to section 4) in FIG. 1 is provided with threads 73 and with channel-like recesses 74 extending parallel to the threads, which recesses are provided in the lower area of the corresponding tread. The channel-like recess 74 allows the glass ionomer cement applied to the circular surface of the pin section 72 to flow away.

Figure 21:
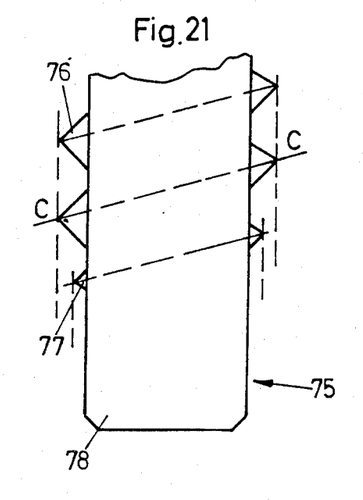
FIG. 21 is a special embodiment of the screw thread of the pin shaft to be screwed into the tooth substance, in a longitudinal section.
Figure 22:
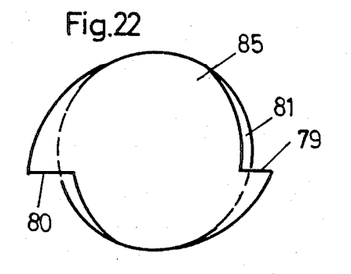
FIG. 22 is a sectional view of the device according to FIG. 21 along line C—C.

A further embodiment of a lower section 75 of the retention pin is shown in FIG. 21. Threads 76 in the lower area join one or several threads 77 with smaller diameter so that a thread 77 practically is used for making a first cut of the thread when screwing the retention pin into the tooth. Furthermore, the lowermost end 78 of pin 75 is formed purely cylindrical so taht when inserting the pin into the bore hole the lower cylindrical extension of the pin is used as a guide. In order to improve screwing a retention pin into the bore of a tooth, within the lower thread or threads, as shown in FIG. 22, the thread is provided with a cutting edge, which extends in a radial direction. Preferably, two cutting edges 79, 80 are formed diametrically opposite to each other. The outer restriction of the cutting edge corresponds to the outer diameter of the thread, the inner restriction is chosen so that a hollow space 61 is provided for taking up the boring chips.

Figure 23:
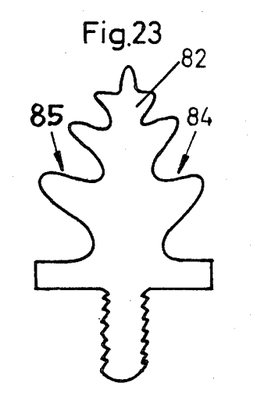
FIG. 23 is a further embodiment of a retention pin with macroscopic shapes within the upper section.
Figure 24:
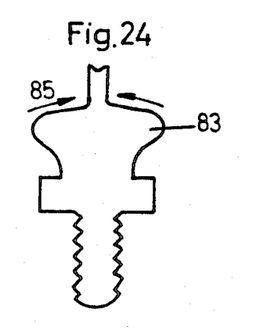
FIG. 24 is a further embodiment of a retention pin with macroscopic shapes on the upper section.

FIGS. 23 and 24 show macroscopic shapes for the upper section of a retention pin schematically. In FIG. 23 this shape is formed as a fish-bone shape, whereas according to the embodiment of FIG. 24 a button shape 83 is shown. Both shapes are used for taking up stresses within the filling structure; the stresses are shown by arrows 84, 85.

What I claim is:

1. Dental retention pin comprising a first section to be inserted into the tooth substance and a second section extending into the filling structure and improving its retention to the tooth, wherein the retention pin is provided with a closed cylindrical or cup-shaped coating at least on said second section for increasing or alternatively improving the retention force, which coating includes at least one bond assisting layer, which undergoes a chemical or physical-chemical bond with the pin material and the material of the filling structure, is applied to the pin and is resistive to the wet conditions within the mouth.

2. A dental retention pin according to claim 1, wherein said bond assisting layer is applied onto the pin, and further comprising a plastics layer, glass ionomer cement layer or further bond assisting layer for improving the bond to the filling structure and having reactive groups on its outmost layer, applied onto the bond assisting layer, said plastics layer, glass ionomer cement layer or further bond assisting layer undergoing a chemical bond to the first-mentioned bond assisting layer and to the filling structure, which is erected upon the completed pin, and wherein one of the applied layers is formed in such a manner that it shrinks cylindrically and results in bracing the pin.

3. Dental retention pin according to claim 1 wherein the bond assisting layer is a single layer of porcelain or a corresponding dental-ceramic mass.

4. A dental retention pin according to claim 1, wherein the bond assisting layer is a metal oxyde layer firmly bonded to the metal pin, and wherein the bond assisting layer and said oxyde layer are formed on the pin in such a manner that a chemical bond is obtained, which is resistive to the wet conditions of the mouth.

5. A dental retention pin according to claim 1, wherein the retention pin is made of a metal having high stability, being biocompatible and having an outer oxyde layer of the same material, and wherein a bond assisting layer of the same or a similar metal is applied onto said pin, and the cylindrical surface of the pin being roughened for improving the forming of an oxyde layer.

6. A dental pin according to claim 1, wherein the first section of the retention pin, which is to be inserted into the tooth substance, and which preferably on its cylindrical surface is provided with a thread or a similar structure, is a metal oxyde layer, which together with a glass ionomer cement layer applied onto the surface of the bore hole receiving the retention pin undergoes a chemical bond.

7. Detnal retention pin according to claim 1, wherein the retention pin is a metal pin, a porcelain pin, a ceramic pin, f.e. made of sintered aluminum oxyde, a plastics pin, f.e. made of hydroxylapatite or tricalcium phosphate, a glass fiber pin or the like.

8. A dental retention pin according to claim 4, wherein a coacting material selected from the group consisting of porcelain, $SiO_2$, $Al_2O_3$, an oxyde of Ca, an oxyde of K, an oxyde of Na, an oxyde of Br is applied onto the metal oxyde, whereby for improving the bond of the porcelain or the dental ceramic mass bond assisting layers are provided underneath, which are known per se in the field of dental veneer crowns.

9. A dental retention pin according to claim 5, wherein a bond assisting layer selected from the group consisting of tin oxide and silane is applied onto the metal oxyde, which bond assisting layer reacts with the metal oxyde.

10. Dental retention pin according to claim 5, wherein a tin oxyde layer is applied to the retention pin, a tin bond consisting layer is applied to the tin oxyde layer, and a plastics layer is applied onto the tin bond assisting layer, which plastics layer is formed as an opaquer.

11. Dental retention pin according to claim 2, wherein the bond assisting layer is a siliciumoxyde carbon layer $SiO_xC$, which is applied to the metal pin by a chemical reaction and results in a preferably adhesive bond, and upon the silicium oxyde carbon layer a silane bond assisting layer is applied, onto which an opaquer layer and/or an outermost layer formed as a plastics layer, glass ionomer cement layer or the like is applied, whereby the opaquer layer and the outermost layer can be one single layer.

12. A dental retention pin according to claim 2, wherein a silane bond assisting layer is applied to a silicium-oxyde-carbon layer ($SiO_xC$-layer), and upon said silane bond assisting layer a further layer is applied, which includes filling material of silicate glasses selected from the group consisting of Ca, Na, Al or Fl, which glasses result in a chemical bond to the glass ionomer cement of the filling material.

13. Dental retention pin according to claim 2, wherein the bond assisting layer is a coating lacquer as a solution of amines, alcydes or resole resins with colouring substances, in heat-setting or cold-setting form, for example $EB_3$ lacquer, or an epoxy-resin, and wherein the bond assisting layer and/or opaquer are applied in one or in several layers.

14. Dental retention pin according to claim 2, wherein the outer layer of the coating, which forms the transient layer for the filling structure, is a plastics material, the internal stability, fracture stability, tension stability and pressure stability of which corresponds to the material of the filling structure, which is or can be made opaque, which has long term reaction capability, which is heat-indifferent and/or which is shrinkable onto the pin, whereby the outer layer has lateral chains or reactive groups to the filling material, which bond with the free chains or reactive groups of the filling structure.

15. Dental retention pin according to claim 2, wherein an attenuation layer of soft material, such as a tin-oxyde layer is applied cylindrically onto the pin.

16. Dental retention pin according to claim 2, wherein one of the layers applied to said pin, preferably the outermost layer, which is formed as the plastics layer, is provided with fibres, filling bodies or the like for controlling the rigidity and the stability of the layer.

17. A dental retention pin according to claim 2, wherein the pin is formed of unnoble metal, has a coating from a layer of noble metal, and on top thereof a layer of tin of about 0.5–50 μm thickness and on top thereof a noble layer.

18. A dental retention pin comprising a first section to be inserted into the tooth substance, a second section extending into the filling structure and improving the retention to the tooth, and a flange between the first and the second section for contacting the tooth substance, wherein the outer layer of the pin is provided as a screw head for receiving an insertion tool, the head of which tool or alternatively the shaft of the pin having a breaking point at which the tool head is separated from the shaft.

19. A dental retention pin according to claim 18, wherein the outer layer of the pin is provided with a screw head for receiving an insertion or screwing tool, said tool and said screwing head being formed as a one-piece unit, which has a breaking point at the tool head or on the shaft of the pin.

20. A dental retention pin according to claim 18 or 19, wherein the shaft of the tool is flexible.

21. Dental retention pin according to claim 18, wherein the flange on its surface facing the tooth substance is upwardly inclined from the outer side towards the shaft of the pin, 22. Dental retention pin according to claim 18, wherein the thread of the shaft of the retention pin has a channel-like recess at the transition from the lower flank of the thread to the shaft of the pin, which recess extends along the thread.

23. A dental retention pin according to claim 18, wherein at least the last thread at the shaft end of the retention pin are provided with a smaller diameter compared with the main threads.

24. Dental retention pin according to claim 18, wherein the lowermost end of the shaft is cylindrical without any threads and is provided as a centering or guiding section.

25. Dental retention pin according to claim 18, wherein the lowermost thread has cutting edges provided at two diametrically opposite positions, which extend in a radial direction and are provided with recesses extending in the radial direction for receiving the cut chips of material.

* * * * *